(12) United States Patent
Duran et al.

(10) Patent No.: US 11,600,168 B1
(45) Date of Patent: Mar. 7, 2023

(54) SYSTEMS TO INFER IDENTITIES OF PERSONS OF INTEREST RAPIDLY AND ALERT FIRST RESPONDERS

(71) Applicant: MOTOROLA SOLUTIONS, INC., Chicago, IL (US)

(72) Inventors: James C Duran, Palatine, IL (US); Doris E Ford, Arvada, CO (US); Yanyan Hu, Medford, MA (US); Matthew Seeley, Sandy, UT (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 0 days.

(21) Appl. No.: 17/444,757

(22) Filed: Aug. 10, 2021

(51) Int. Cl.
| | |
|---|---|
| *G08B 21/00* | (2006.01) |
| *G08B 27/00* | (2006.01) |
| *G16H 10/60* | (2018.01) |
| *G08B 25/00* | (2006.01) |

(52) U.S. Cl.
CPC ......... *G08B 27/001* (2013.01); *G08B 25/006* (2013.01); *G16H 10/60* (2018.01)

(58) Field of Classification Search
CPC .................................................. G08B 27/001
See application file for complete search history.

(56) References Cited

U.S. PATENT DOCUMENTS

| | | | |
|---|---|---|---|
| 5,861,810 A | 1/1999 | Nguyen | |
| 9,389,083 B1 | 7/2016 | Agulnik et al. | |
| 10,192,070 B1 | 1/2019 | Hodge | |
| 10,885,066 B2 | 1/2021 | Lawlor et al. | |
| 2014/0266699 A1* | 9/2014 | Poder | G08B 25/008 340/539.13 |
| 2015/0081579 A1 | 3/2015 | Brown et al. | |
| 2021/0390808 A1* | 12/2021 | Nilsson | G07C 9/00309 |

* cited by examiner

*Primary Examiner* — Travis R Hunnings

(57) ABSTRACT

Systems, devices, and technical methods of the present disclosure leverage digital visitor logs from confinement facilities to identify people of interest that may be involved in incidents to which first responders are dispatched. When a phone call is received at phone public safety access point, a first query including a name associated with the call is transmitted to a digital visitor log for a confinement facility. A digital response to the first query identifies a visitee who was visited by a visitor by that name while the visitee was in confinement. The visitee's name is then transmitted in a second query to a digital repository containing release records; a digital response indicates the visitee was released before the call was received. An electronic notification that identifies the visitee is transmitted to a device associated with an agent who is responding to the call.

20 Claims, 6 Drawing Sheets

| SUBSTANCE | MEDICATIONS | RECOMMENDED ACTIONS | ACTIONS FROM WHICH TO REFRAIN | FORCE TECHNIQUES FROM WHICH TO REFRAIN | FORCE TECHNIQUES WHICH MAY BE MORE EFFECTIVE |
|---|---|---|---|---|---|
| PHENCYCLIDINE (PCP) | ALPRAZOLAM (XANAX) | REQUESTING AT LEAST FOUR BACKUP UNITS | MAKING LOUD NOISES (E.G., ISSUING LOUD COMMANDS) | STRIKING WITH BATON | USING A TASER |
| | DIAZEPAM (VALIUM) | WEARING GLOVES (PCP IS TRANSDERMAL) | SHINING BRIGHT LIGHTS (E.G., FLASHLIGHTS AND SPOT LIGHTS) | FIRING BEAN BAG ROUNDS | HAVING A DIFFERENT OFFICER HOLD EACH APPENDAGE |
| | | | | | APPLYING HANDCUFFS |
| FENTANYL | NALOXONE | ADMINISTERING OXYGEN, IF NECESSARY | INDUCING VOMITING (MAY CAUSE VOMIT TO BE ASPIRATED) | APPLYING CHOKE HOLDS | APPLYING HANDCUFFS |
| | | ADMINISTERING CPR, IF NECESSARY | SLAPPING OR SHAKING FORCEFULLY | | |
| | | WEARING GLOVES (FENTANYL IS TRANSDERMAL) | | | |

| MENTAL ILLNESS | MEDICATIONS | RECOMMENDED ACTIONS | ACTIONS FROM WHICH TO REFRAIN | FORCE TECHNIQUES FROM WHICH TO REFRAIN | FORCE TECHNIQUES WHICH MAY BE MORE EFFECTIVE |
|---|---|---|---|---|---|
| BIPOLAR DISORDER | PALIPERIDONE (INVEGA) | APPLY DE-ESCALATION TECHNIQUES | MAKING LOUD NOISES (E.G., ISSUING LOUD COMMANDS) | APPLYING CHOKE HOLDS | APPLYING HANDCUFFS |
| | LITHIUM | | ARGUING OR DEBATING | | |
| PARANOID SCHIZOPHRENIA | CHLORPROMAZINE (THORAZINE) | ASKING THE PERSON TO DESCRIBE WHAT IS BEING SEEN OR HEARD, IF PERSON IS HALLUCINATING | ARGUING OR DEBATING | STRIKING WITH BATON | APPLYING HANDCUFFS |
| | FLUPHENAZINE (PROLIXIN) | DISPERSING ANY CROWDS THAT MAYBE WATCHING THE PERSON | | | |

*FIG. 2B*

SYSTEMS TO INFER IDENTITIES OF PERSONS OF INTEREST RAPIDLY AND ALERT FIRST RESPONDERS

BACKGROUND

Emergency calls (e.g., 9-1-1 calls) may be routed to specialized call centers known as public safety answering points (PSAPs). Dispatchers at the PSAPs answer the emergency calls, assess the nature of the emergencies being reported by those calls, and dispatch appropriate emergency-response personnel (e.g., police, firefighters, and paramedics) accordingly.

BRIEF DESCRIPTION OF THE SEVERAL VIEWS OF THE DRAWINGS

In the accompanying figures similar or the same reference numerals may be repeated to indicate corresponding or analogous elements. These figures, together with the detailed description, below are incorporated in and form part of the specification and serve to further illustrate various examples of concepts that include the claimed invention, and to explain various principles and advantages of those examples.

FIG. 2A illustrates a relation that may be used to associate substances with medications, actions, and force techniques, according to one example.

FIG. 2B illustrates a relation that may be used to associate mental illnesses with medications, actions, and force techniques, according to one example.

Figure 1:
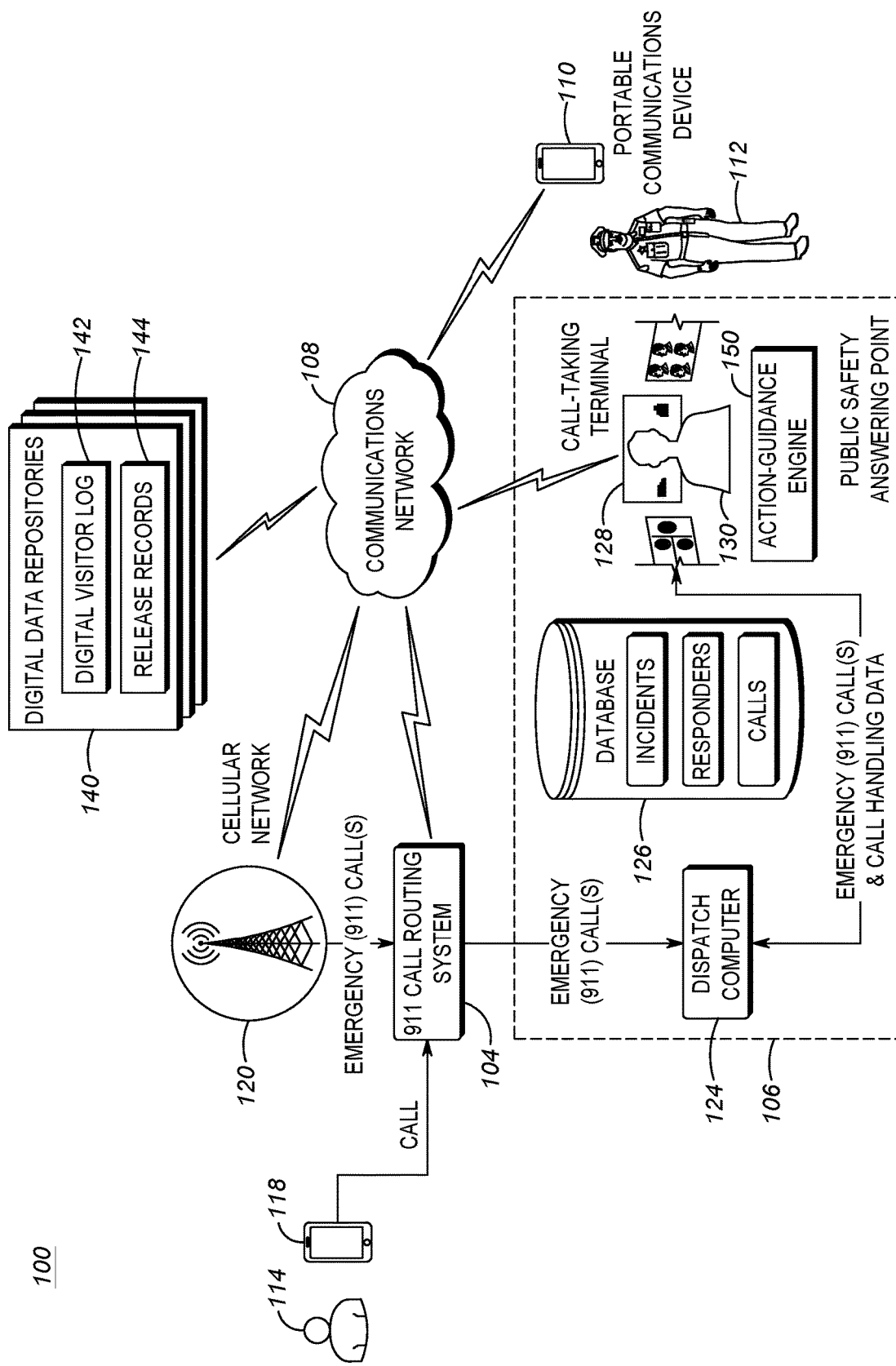
FIG. 1 illustrates an example computing environment in which systems of the present disclosure can operate, according to one example.

Skilled artisans will appreciate that elements in the figures are illustrated for simplicity and clarity and have not necessarily been drawn to scale. For example, the dimensions of some of the elements in the figures may be exaggerated relative to other elements to help improve understanding of examples of the present disclosure.

The system, apparatus, and method components have been represented where appropriate by conventional symbols in the drawings, showing only those specific details that are pertinent to understanding the examples of the present disclosure so as not to obscure the disclosure with details that will be readily apparent to those of ordinary skill in the art having the benefit of the description herein.

DETAILED DESCRIPTION OF THE INVENTION

Law-enforcement personnel (e.g., police officers, sheriff's deputies, and highway patrol officers), paramedics, firefighters, and other first responders who respond to incidents often have incomplete knowledge about the people involved in those incidents. This incomplete knowledge can reduce the chances of positive outcomes for such incidents. Police officers responding to calls that seem innocuous may be unaware that they are likely to encounter individuals with known violent tendencies and may therefore fail to anticipate dangerous physical confrontations. Paramedics, firefighters, or other personnel who respond to medical emergencies may struggle to distinguish between different possible causes of an unfamiliar person's distress and may therefore be unsure of which type of lifesaving treatment to administer to save the person's life.

To further elucidate how a first responder's knowledge about the people involved in an incident may be incomplete, consider the following examples. Suppose an officer who pulls over a speeding vehicle uses an automated license plate reader (ALPR) to determine the license plate number of the vehicle and submits an electronic query to determine the name of the person to whom the vehicle is registered (i.e., the registrant), the make and model of the vehicle, the vehicle identification number (VIN) of the vehicle, and whether or not the vehicle has been reported as stolen. The officer may also submit a second electronic query to retrieve information about the registrant, such as the registrant's driver license information, driving record, home address, date of birth, eye color, and height—or whether there is an active warrant for the registrant's arrest. The officer may thus have access to some information about the registrant before the officer approaches the vehicle.

However, there is no guarantee that the registrant is the person who is actually driving the vehicle. Furthermore, the available information about the registrant generally does not reveal any details about who any passengers in the vehicle may be—and there generally is insufficient time (e.g., usually no more than two minutes) to complete any further investigation to determine who those passengers may be. As a result, the identities of any passengers in the vehicle— including persons with violent criminal records who have recently been released from prison—may be unknown to the officer. As a result, the officer may have too little information to appraise the risk of approaching the vehicle accurately. If an officer underestimates the risk of approaching the vehicle, the officer may be more vulnerable to being surprised if one of the vehicle's occupants physically attacks the officer.

Officers who respond to other types of incidents may face similar risks. For example, suppose an officer is dispatched to a residential house to perform a welfare check, defuse a domestic dispute, or investigate suspicious activity. The dispatcher may look up the owner of the home based on real property records, submit a query to a database to determine whether the owner has a criminal history or an outstanding warrant, and provide the query results to the officer. However, since time for further investigation is generally very limited (e.g., because the average police response time is usually less than fifteen minutes), the dispatcher might not be able to provide the officer with much additional information about who else might be present at the home— including recently released convicts and people with documented mental illnesses—before the officer arrives at the scene. As a result, the officer may have too little information to appraise the risk of approaching the house accurately or to ascertain what actions may be prudent (or imprudent) to address the situation.

Paramedics or firefighters may be similarly impeded by incomplete knowledge when responding to medical emergencies. A dispatcher may be able to look up the owner of a home or the registrant of a vehicle where a medical emergency is taking place, but there is no guarantee that a person who is in distress at the location in question is the owner or registrant. Suppose, for example, that paramedics arrive at a scene where an agitated person is speaking incoherently. The person's behavior may be the result of a substance overdose (e.g., of methamphetamine), a mental illness, or even a combination thereof; without more information about the person, it may be difficult for the paramedics to infer what the cause of the person's behavior is likely to be. If the paramedics cannot reasonably infer the cause due to the incomplete information that is available about the person, the paramedics may assume an inaccurate cause of the behavior. The incorrect assumption, in turn, may lead the paramedics to administer a type of treatment to the person that will not be effective—or may even exacerbate the person's condition. For example, if the paramedics assume that the behavior is caused by a mental illness rather than a drug overdose, the paramedics may administer a medication for mental illness that interacts with the drug in a manner that is harmful to the person. Furthermore, since time is of the essence in medical emergencies, the delay that results from administering the wrong medication and waiting to see if the medication is effective could further endanger the person. In addition, if the person is under the influence of a transdermal drug such as phencyclidine (PCP) or Fentanyl, the paramedics may unknowingly endanger themselves by letting their skin make contact with the person's skin.

Thus, for the safety of first responders and the people they serve, many advantages can be provided by a technical method, device, and system that can rapidly identify people of interest that first responders may be likely to encounter during an incident—specifically, people of interest who might not be directly associated (e.g., in databases that list automobile registrants, home occupants, or phone-number registrants) with a street address where the incident occurs, an automobile involved in the incident, or a phone number used to place an emergency call in response to the incident. In addition, many advantages could be provided by technical methods, systems, and devices that can further recommend actions that the first responder should prepare to take based on the identities and histories of those people of interest.

Systems, devices, and technical methods of the present disclosure leverage digital visitor logs from confinement facilities (e.g., jails, prisons, penitentiaries, and psychiatric hospitals) to identify people of interest that may be involved in incidents to which first responders are dispatched. The systems disclosed herein expand the capabilities of PSAP infrastructures and devices associated with first responders (e.g., mobile devices) by allowing those devices to alert first responders about the identities of those people of interest and the nature of previous events that caused those persons of interest to be confined. Systems described herein can also configure the devices associated with the first responders to provide risk scores based on the previous events and the nature of the current incident to which the first responders are being dispatched. Furthermore, systems described herein can configure those devices to recommend specific actions for the first responders to take based on the previous events. The systems described herein employ multiple technologies to achieve these enhanced device capabilities rapidly, such as digital data repositories, processors, and wireless transceivers. Since time is frequently of the essence for first responders, the speed with which the systems described herein achieve the functionality described herein is advantageous; performing the functions described herein without employing at least the technologies described herein would consume too much time to be helpful for first responders.

Further advantages and features consistent with this disclosure will be set forth in the following detailed description with reference to the figures.

FIG. 1 illustrates an example computing environment 100 in which systems of the present disclosure can operate, according to one example. As shown, the computing environment 100 includes a 911 call routing system 104, and a public safety answering point (PSAP) 106. The 911 call routing system 104 and the PSAP 106 are communicatively coupled to one another via a communications network 108. The communications network 108 includes wireless connections, wired connections, or a combination thereof. The communications network 108 may be implemented using, for example, a wide area network, the Internet (including public and private Internet Protocol (IP) networks), a Long Term Evolution (LTE) network, a Global System for Mobile Communications (or Groupe Special Mobile (GSM)) network, a Code Division Multiple Access (CDMA) network, an Evolution-Data Optimized (EV-DO) network, an Enhanced Data Rates for Global Evolution (EDGE) network, a Third Generation Partnership Project (3GPP) network, a 4G network, a 5G network, a landline telephonic network, a Low Earth Orbit (LEO) network (e.g., for satellite phones), a Geosynchronous Orbit (GEO) network (e.g., for satellite phones), and one or more local area networks (e.g., a Bluetooth™ network or a Wi-Fi network) or a combinations thereof.

As described in detail herein, the PSAP 106 is configured to receive emergency calls routed by the 911 call routing system 104. A caller 114 (e.g., a civilian) may place an emergency call (for example, by dialing 9-1-1) using a telephone 118. The telephone 118 may be a cellular phone (e.g., a smart phone), a satellite phone, a Voice over Internet Protocol (VoIP) phone, a landline telephone, or some other type of communications device.

In examples in which the telephone 118 is a cellular phone, the telephone 118 includes hardware and software configured to communicate via the cellular network 120.

The cellular network 120 may operate according to an industry standard cellular protocol such as the Long Term Evolution (LTE) standard (including LTE-Advanced or LTE-Advanced Pro compliant with, for example, the 3GPP Technical Specification (TS) 36 series), the 5G standard (including a network architecture compliant with, for example, the 3GPP TS 23 series and a new radio (NR) air interface compliant with the 3GPP TS 38 series), or some other industry standard. The cellular network 120 may also facilitate the use of applications that implement mobile alliance (OMA) push to talk (PTT) over cellular (OMA-PoC), VoIP, or PTT over IP (PoIP).

A call placed via the cellular network 120 or some other component of the communications network 108 may be routed to the 911 call routing system 104. The 911 call routing system 104 represents the hardware and telecommunications infrastructure of a 911 system. The 911 call routing system 104 may include aspects of an Enhanced 911 (E911) system, a Next Generation 911 (NG911) system, or both. The 911 call routing system 104 operates to receive emergency calls and route those calls to the PSAP 106 or some other PSAP based on the caller's current location (e.g., as determined using a geolocation system of the telephone 118 or as stated by the caller verbally).

The PSAP 106 may include a dispatch computer 124, a database 126, and a call-taking terminal 128. The dispatch computer 124, database 126, and call-taking terminal 128 are communicatively coupled using one or more wired and/or wireless networks (not shown). A dispatcher 130 interacts with the call-taking terminal 128 to answer communications (e.g., calls) received at the PSAP 106 and to access and modify data stored in the database 126. The PSAP 106 performs computer aided dispatch (CAD) operations for law enforcement and other emergency services.

Persons of skill in the art will recognize that an in-depth discussion of how computer aided dispatch operations is beyond the scope of this disclosure.

Calls or other communications may be received at the PSAP 106 via a component of the communications network 108 (e.g., the cellular network 120) or the 911 call routing system 104. In some examples, the PSAP 106 sends and receives other types of voice communications (e.g., two-way radio communications) and data communications (e.g., short message service (SMS) messages, multimedia message service (MMS) messages, email messages, pages, or instant messages).

The dispatch computer 124 may includes a processor (e.g., a microprocessor) programmable device), a memory (e.g., a computer-readable storage medium), an input/output interface (not shown), and various other hardware and software components for performing computer aided dispatch, call control, and other operations at the PSAP 106.

The dispatch computer 124 is communicatively coupled to the call-taking terminal 128. The call-taking terminal 128 may include one or more input/output (I/O) devices, such as displays (e.g., monitors), keyboards, keypads, computer mice, joysticks, touch screens, speakers, microphones, and headsets. The dispatch computer 124 receives input from and provides output (e.g., audio output for calls) to the dispatcher 130 through the call-taking terminal 128. The dispatch computer 124 and the call-taking terminal 128 are capable of controlling call handling hardware and software (not shown) to originate and terminate voice calls (e.g., emergency calls), and other forms of electronic communication either alone or by interfacing with components of the communications network 108 and other communications networks.

The dispatch computer 124 is communicatively coupled to, and writes data to and from, the database 126. As shown in FIG. 1, the database 126 may be housed on a suitable database server communicatively coupled to the dispatch computer 124. In other examples, the database 126 may be part of a cloud-based database system (for example, a data warehouse) external to the computing environment 100 and accessible by components of the computing environment 100 via the communications network 108. Also, some of the database 126 may be locally stored on the dispatch computer 124.

The dispatch computer 124 may use data stored in the database 126 and received from members of the public (e.g., the caller 114), first responders (e.g., the first responder 112), and other sources to dispatch first responders and other personnel in response to calls. In some examples the database 126 electronically stores incident data, responder data, and call data.

Incident data refers to incident records for public safety incidents. An incident record may include a data structure within the database 126 which contains information regarding a public safety incident. An incident record may also include unstructured data (e.g., natural-language text). In some examples, the database 126 may store the incident data in a CAD incident database. As used herein, the term "incident" refers to a matter in response to which a first responder may be dispatched. For example, an incident may be a crime (e.g., theft, robbery, etc.). An incident may also be a medical emergency (e.g., a heart attack, a drug overdose, or a serious injury), a fire, a request for assistance to locate a missing person, or some other matter for which it is prudent to dispatch one or more types of first responders. The incident data for an incident may include an incident type (e.g., a crime, a fire, a medical emergency, a natural disaster, or a traffic stop), an incident identifier (e.g., an alphanumeric code that identifies the incident record within a computer-aided dispatch system), call identifiers that identify emergency and non-emergency calls received related to the incident, and other types of data associated with the incident.

Examples of responder data may include responder identifiers (e.g., name, rank, and agency), an active incident assignment for a responder, a responder role (e.g., a supervisory role or an area of operation overall or within the incident), a responder location, responder equipment data (e.g., model, configuration, and responder assignment information for portable communications devices).

Call data may include data for calls (e.g., emergency calls) routed to the PSAP 106. Some examples of call data include a call identifier (e.g., an alphanumeric code that identifies the call record within a computer-aided dispatch system), an incident assignment associating the call with an incident, a location from which the call was placed, a caller identifier (e.g., a name) that identifies the caller that placed the call, and a phone number of the telephone used to place the call.

The dispatcher 130 may be trained to handle incident communications. As noted above, these communications can include voice communications (e.g., voice calls) and data communications (e.g., text messages, email messages, pages, and the like). Based on the received communications, the dispatcher 130 may dispatch the appropriate first responders to handle incidents reported by callers. In addition, the dispatch computer 124 may be configured to dispatch the appropriate first responders automatically. The dispatch computer 124 and the call-taking terminal 128 may also receive data input from the dispatcher 130 and save the data input to the database 126. Generally, regardless of how or when an individual communicates with the PSAP 106 about an incident, information about the communication is stored in the database 126.

The computing environment 100 further includes digital data repositories 140 that are accessible to the PSAP 106 via the communications network 108. The digital data repositories 140 include a digital visitor log 142 for a confinement facility (e.g., a jail, a prison, a penitentiary, a psychiatric hospital, or some other institution where people may be confined). The digital visitor log 142 contains data such as names, phone numbers, and other identifying information of people (i.e., the visitors) who have visited persons confined in the confinement facility (i.e., the visitees). A visitee may be an inmate at a prison, for example, and a visitor may be the inmate's friend, spouse, parent, sibling, or pastor. The digital visitor log 142 may also include license plates, VIN numbers, or other data that identifies vehicles that have been used to visit the confinement facility (e.g., vehicles in which visitors arrived at the confinement facility or departed from the confinement facility). The digital data repositories 140 also include release records 144 for the confinement facility. The release records 144 may include dates and times that specify when persons confined at the facility (e.g., visitees) were released from the confinement facility. Note that the digital visitor log 142 includes data that identifies visitors who came to pick up the persons who were released and data that identifies the vehicles used by the visitors to pick up the released persons.

As one example of how systems disclosed herein may operate, consider the following example. Suppose the caller 114 places a call via the telephone 118 and the 911 call routing system 104 routes the call to the PSAP 106. A Calling Name Presentation (CNAM) function of a caller identification (Caller ID) service can be used to determine to whom the telephone is registered. Furthermore, the caller 114 may state the name of the caller 114 verbally (which may or may not be the name of the person to whom the telephone 118 is registered). Either or both of these names (e.g., the name provided by the CNAM function or the name provided by the caller) can be said to be associated with the call and used to form a first query. The name associated with the call is transmitted in the first query to the digital visitor log 142 via the communications network 108. The first query may be transmitted automatically by the dispatch computer 124 or by the dispatcher 130 at the call-taking terminal 128.

In response to the first query, the digital visitor log 142 sends a digital response via the communications network 108. The digital response indicates that a visitor, who is identified by the name associated with the call, visited a visitee (e.g., an inmate) at the confinement facility while the visitee was confined at the confinement facility.

In addition or alternatively, the PSAP 106 may receive a digital identifier of a vehicle associated with an incident. The digital identifier may be included in the first query that is transmitted to the digital visitor log 142 via the communications network 108. In this example, the response to the first query may indicate that the vehicle was used by a visitor who visited a visitee at the confinement facility while the visitee was confined at the confinement facility. Thus, the digital identifier of the vehicle may be used to identify the visitee by association. The first responder 112, for example, may be a police officer or a highway patrol officer who pulls over the vehicle for a moving violation (e.g., speeding, expired inspection tags, or running a red light). In this example, the observed moving violation may be the incident with which the vehicle is associated. The first responder 112 may use an automated license plate reader (ALPR) to determine the license plate number of the vehicle and transmit the license plate number to the PSAP 106 (e.g., via the portable communications device 110). In this example, the license plate number would serve as the digital identifier of the vehicle and would be included in the first query that is sent to the digital visitor log 142.

Once the visitee is identified, the name of the visitee is transmitted in a second query via the communications network 108 (e.g., from the dispatch computer 124 or the call-taking terminal 128) to the digital data repositories 140 for comparison against the release records 144 for the confinement facility. The second query may also request additional information that may be available about the visitee in the digital data repositories 140, such as data describing a previous event that involved the visitee such that the visitee was confined in the confinement facility as a result of the previous event (e.g., a crime for which the visitee was convicted and sentenced to confinement or a psychological event for which the visitee was confined).

In response to the second query, the digital data repositories 140 send a digital response that indicates the visitee was released from the confinement facility before the call was received (e.g., by providing a release date and time that preceded the call). The digital response may further indicate a type of the previous event.

In some examples, once the digital response is received at the PSAP 106, software running at the dispatch computer 124 or the call-taking terminal 128 may verify that an amount of time that elapsed between when the visitee was released from the confinement facility and when the call was received meets a threshold (e.g., to ensure the visitee's release from the confinement facility was recent enough to be relevant for the first responder 112). In one example, the threshold amount of time may be one year and the threshold is considered to be met if the amount of time elapsed is less than one year.

After the digital response is received at the PSAP 106, an electronic notification that includes data that identifies the visitee (e.g., the visitee's name, a digital image of the visitee, etc.) is sent to an electronic device associated with an agent that is responding to the call (e.g., via the communications network 108). For example, the dispatcher 130 may be the agent responding to the call and the call-taking terminal 128 may be the device associated with the agent. In addition or alternatively, if the first responder 112 is dispatched in response to the call, the first responder may be the agent responding to the call and the portable communications device 110 (e.g., a smart phone or a two-way radio) may be the device associated with the agent. The electronic notification may further indicate a type of the previous event for which the visitee was confined in the confinement facility. In examples in which the amount of time elapsed since the release of the visitee is compared to a threshold amount of time, the electronic notification may be sent after verifying that the amount of time elapsed meets the threshold.

In addition, the Action-Guidance engine 150 may determine a prescriptive action to recommend to the first responder 112 based on the type of the previous event. The action-guidance engine 150 is a unit of software that is executed by a processor and memory (e.g., in the dispatch computer 124, in the call-taking terminal 128, or via a cloud-computing service accessed through the communications network 108). A prescriptive action recommended by the action-guidance engine 150 can be included in the electronic notification.

For example, suppose that the type of the previous event indicates that the visitee has been associated with illicit use of a substance (e.g., the visitee was caught possessing a narcotic, failed a drug test, or was hospitalized due to a drug overdose). In this example, the action-guidance engine 150 may identify the type of substance that is associated with the visitee via the previous event and compare the type of the substance to a relation that associates the substance with a medication (e.g., an antidote) that can be used to counteract an effect of the substance. The relation may further associate the substance with an action that is likely to trigger aggressive behavior in persons who are under the influence of the substance and with force techniques that are likely to be ineffective for subduing persons who are under the influence of the substance. In this example, the prescriptive action recommended by the action-guidance engine 150 for the first responder 112 may include bringing at least one dose of the medication that can be used to counteract an effect of the substance to the location where the first responder 112 is dispatched as a result of the call. The prescriptive action may also include refraining from performing the action that is likely to trigger aggressive behavior in persons who are under the influence of the substance and refraining from applying a force technique that is likely to be ineffective for subduing persons who are under the influence of the substance.

In another example, suppose that the type of the previous event indicates that the visitee suffers from a mental illness (e.g., the visitee was involuntarily institutionalized as a result of an episode of delusional paranoia, severe mania, or hallucinations). In this example, the action-guidance engine 150 may identify the type of the mental illness that is associated with the visitee via the previous event and compare the type of the mental illness to a relation that associates the mental illness with a medication that can be used to counteract an effect of the mental illness. The relation may further associate the mental illness with an action that is likely to trigger aggressive behavior in persons who suffer from the mental illness and with force techniques that are likely to be ineffective for subduing persons who suffer from the mental illness. In this example, the prescriptive action recommended by the action-guidance engine 150 for the first responder 112 may include bringing at least one dose of the medication that can be used to counteract an effect of the mental illness to the location where the first responder 112 is dispatched as a result of the call. The prescriptive action may also include refraining from performing the action that is likely to trigger aggressive behavior in persons who suffer from the mental illness and refraining from applying a force technique that is likely to be ineffective for subduing persons who suffer from the mental illness.

In some examples, the action-guidance engine 150 may determine a risk score based on the type of the previous event and based on a type of an incident reported in the call (or the type of the incident associated with the vehicle, if the first query included data describing a vehicle). If the risk score satisfies a predefined condition (e.g., is greater or equal to a threshold score if the score is quantitative or equals a predefined value such as "high" if the risk score is categorical), the action-guidance engine 150 may cause an additional electronic notification to be transmitted to the portable communications device 110 or to the call-taking terminal 128. The additional electronic notification may advise the first responder 112 or the dispatcher 130 to request that additional agents assist the first responder 112 or the dispatcher 130 in responding to the call or incident. If the first responder 112 is a police officer, for example, and the type of the previous event or the incident is a violent felony additional electronic notification may advise the police officer or the dispatcher 130 to call for backup.

There are many different methods that can be devised for determining a risk score. For example, in a categorical scheme, if the type of the previous event is a violent felony (e.g., homicide, robbery, kidnapping, aggravated assault) and the type of the incident is also a violent felony, the value "high" may assigned as the risk score. If neither the type of the previous event nor the type of the incident is a felony, then the value "low" may be assigned as the risk score. If the type of the previous event is a violent felony and the type of the incident is not a felony, then the value "medium" may be assigned as the risk score. If the type of the incident is a violent felony and the type of the previous event is not a felony, then the value "high" may be assigned as the risk score.

In another example, the risk score may be determined based on the amount of time that has elapsed since the visitee was released from the confinement facility and the time when the call was received (or the commencement of the incident as measured in some other way, such as when an ALPR system retrieved a license plate for a vehicle that is being pulled over for a moving violation). Criminal recidivism rates are generally high during the first year after criminals are released from confinement. The recidivism rate tends to decline over time, although the rate of the decline tends to level off over time. Thus, convicts who were released more recently might be considered a greater risk than convicts who were released less recently, but the decrease in the risk level is not linear (e.g., the risk level should not converge to zero). A method that hydridizes an exponential regression approach and a cubic-spline interpolation approach can be used to create a weight function that can be used to help ensure that risk scores reflect recidivism trends over time (neither approach alone approximates the recidivism curve as well as this hybridized approach). For example, a weighting function W(x) can be defined as:

$$W(x) = \frac{(52.67 \cdot 0.99^x) + (1.36 \cdot 10^{-5} \cdot x^3) - (2.22 \cdot 10^{-62} \cdot x^2) - 0.348x + 56.10}{2}$$

where x is the number of weeks that have elapsed since the time when the visitee was released from confinement and the time when the call was received (or when some other event signifying the commencement of the incident occurred). Although this example function is based on empirical research published in 2018, persons of skill in the art will recognize that similar hybridized functions may be developed based on subsequent research. The risk score can be defined as W(x) can multiplied by a sum of sub-scores that are determined by the type of the previous event and the type of the incident such that:

Risk Score=$W(x) \cdot (p+i)$, where p represents the sub-score for the type of the previous event and i represents the sub-score for the incident type. For example, a violent felony may be assigned a sub-score of two, a non-violent felony may be assigned a sub-score of one, and a misdemeanor may be assigned a sub-score of ½. For example, suppose the time elapsed between the visitee's release from confinement and the commencement of the incident (e.g., the time when the call was received) is three weeks. Also suppose that the type of the previous event is a violent felony and the type of the incident is a misdemeanor. In this example, the risk score would be defined as W(3) multiplied by the sum of one half and two. Persons of skill in the art will recognize that other sub-scoring schemes can be used without departing from the spirit and scope of this disclosure.

FIG. 2A illustrates a relation 202 that may be used to associate substances with medications, actions, and force techniques, according to one example. Specifically, relation 202 associates substances with medications that can be used to counteract effects of the substances. The relation 202 also associate substances with recommended actions, actions that are likely to trigger aggressive behavior in persons who are under the influence of the substances, and force techniques that are likely to be ineffective for subduing persons who are under the influence of the substances.

FIG. 2B illustrates a relation 204 that may be used to associate mental illnesses with medications, actions, and force techniques, according to one example. The relation 204 associates mental illnesses with medications that can be used to counteract effects of those mental illnesses. The relation 204 also associates mental illnesses with recommended actions, actions that are likely to trigger aggressive behavior in persons who suffer from the mental illnesses, and force techniques that are likely to be ineffective for subduing persons who are afflicted by the mental illnesses.

Persons of skill in the art will recognize that the relation 202 and the relation 204 may be stored electronically in any combination of different data structures such as objects (e.g., in object-oriented programming languages), arrays, records (e.g., in TurboPascal), hash tables, vectors (e.g., in C++), and tables (e.g., in Structured Query Language (SQL)).

As explained above with respect to FIG. 1, the action-guidance engine 150 may use a relation such as the relation 202 or the relation 204 to identify prescriptive actions for the first responder 112 once any substances or mental illnesses associated with the visitee have been identified. Persons of skill in the art will understand the relation 202 and the relation 204 are provided as illustrative examples; other relations that associate additional substances or mental illnesses with additional medications, actions, and force techniques can be used without departing from the spirit and scope of this disclosure.

Figure 3:
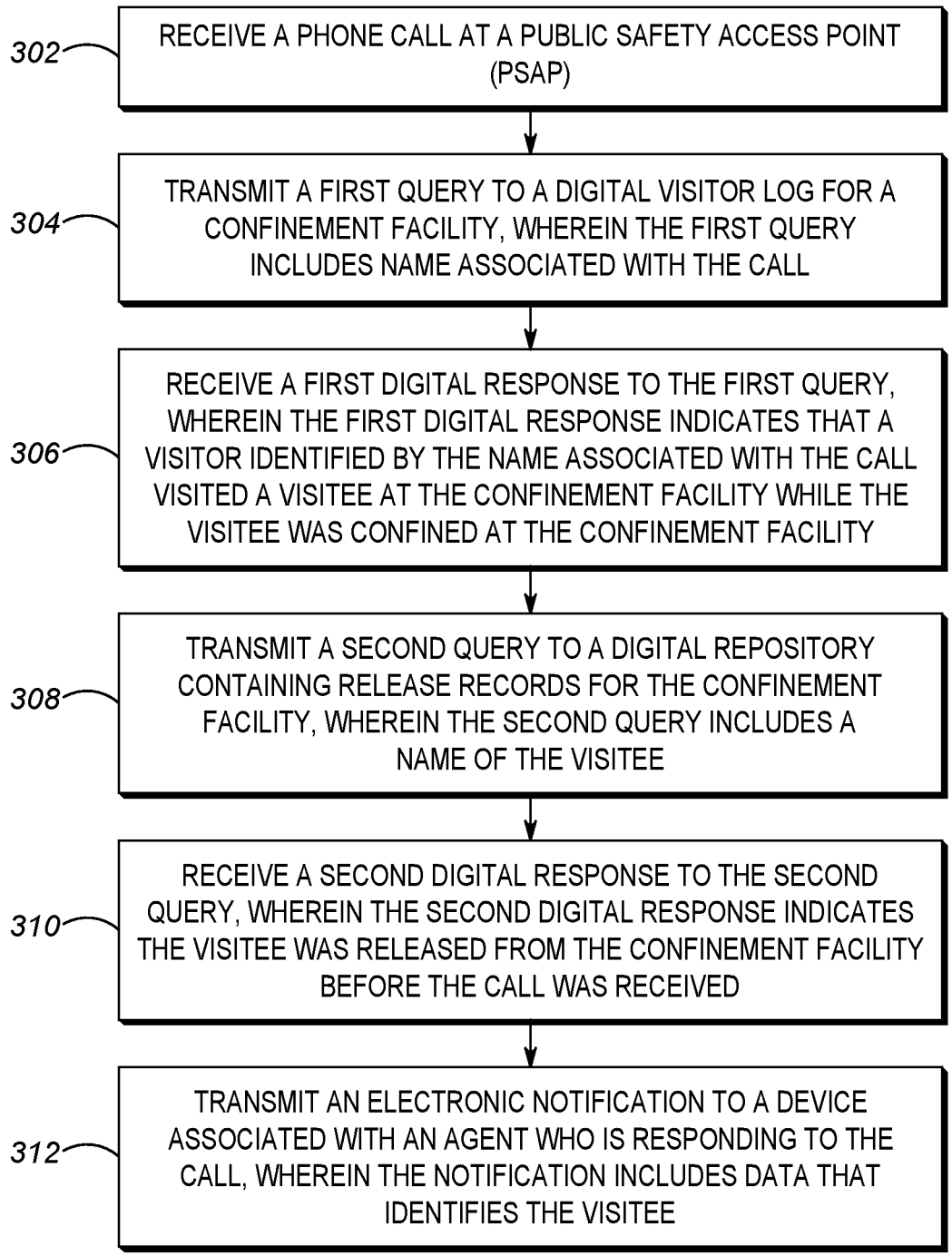
FIG. 3 illustrates functionality for systems disclosed herein, according to one example.

FIG. 3 illustrates functionality 300 for systems disclosed herein, according to one example. The functionality 300 does not have to be performed the exact sequence shown. Also, various blocks may be performed in parallel rather than in sequence. Accordingly, the elements of the functionality 300 are referred to herein as "blocks" rather than "steps." The functionality 300 can be executed as instructions on a machine (e.g., by one or more processors), where the instructions are stored on a transitory or non-transitory computer-readable storage medium. While only six blocks are shown in the functionality 300, the functionality 300 may comprise other actions described herein. Also, in some examples, some of the blocks shown in the functionality 300 may be omitted without departing from the spirit and scope of this disclosure.

As shown in block 302, the functionality 300 includes receiving a phone call at a public safety access point (PSAP). The phone call may originate from a cellular phone (e.g., a smart phone), a satellite phone, a Voice over Internet Protocol (VoIP) phone, a landline telephone, or some other type of communications device.

As shown in block 304, the functionality 300 includes transmitting a first query to a digital visitor log for a confinement facility, wherein the first query includes name associated with the call. The name associated with the call may be, for example, provided verbally by a caller (e.g., in response to an inquiry by a dispatcher who answers the call) or a name of a person to whom a phone used to place the call is registered (e.g., as determined by a CNAM function of a Caller ID service). The confinement facility may be a jail, a prison, a penitentiary, a psychiatric hospital, or some other institution where people may be confined. The first query may be transmitted to the digital visitor log via an electronic communications network.

As shown in block 306, the functionality 300 includes receiving a first digital response to the first query, wherein the first digital response indicates that a visitor identified by the name associated with the call visited a visitee at the confinement facility while the visitee was confined at the confinement facility. The digital response to the first query provides the name of the visitee. The digital response to the first query may be received via an electronic communications network.

As shown in block 308, the functionality 300 includes transmitting a second query to a digital repository containing release records for the confinement facility, wherein the second query includes a name of the visitee. The second query may be transmitted to the digital repository via an electronic communications network.

As shown in block 310, the functionality 300 includes receiving a second digital response to the second query, wherein the second digital response indicates the visitee was released from the confinement facility before the call was received. The second digital response may be received via an electronic communications network.

As shown in block 312, the functionality 300 includes transmitting an electronic notification to a device associated with an agent who is responding to the call, wherein the notification includes data that identifies the visitee. The data that identifies the visitee may comprise the visitee's name, a digital image of the visitee, and other data that may be used to identify the visitee. The electronic notification may further indicate a type of a previous event that involved the visitee, wherein the visitee was confined in the confinement facility as a result of the previous event. Prior to transmitting the electronic notification, the functionality 300 may also include verifying that an amount of time that elapsed between when the visitee was released from the confinement facility and when the call was received meets a threshold.

In addition, the electronic notification may further include a prescriptive action for the agent based on a type of the previous event. For example, if the type of the previous event indicates that the visitee has been associated with illicit use of a substance, the prescriptive action may include bringing a medication that can be used to counteract an effect of the substance, refraining from an action that is likely to trigger aggressive behavior in persons who are under the influence of the substance, or refraining from applying a force technique that is likely to be ineffective for subduing persons who are under the influence of the substance.

In another example, if the type of the previous event indicates that the visitee suffers from a mental illness, the prescriptive action may include bringing a medication that can be used to counteract an effect of the mental illness, refraining from an action that is likely to trigger aggressive behavior in persons who suffer from the mental illness, or refraining from applying a force technique that is likely to be ineffective for subduing persons who suffer from the mental illness.

The functionality 300 may further include determining a risk score based on a type of the previous event and a type of an incident reported in the call; and upon determining that the risk score satisfies a predefined condition, sending an additional electronic notification to the device associated with the agent. The additional notification may advise the agent to request that additional agents assist the agent in responding to the call.

Figure 4:
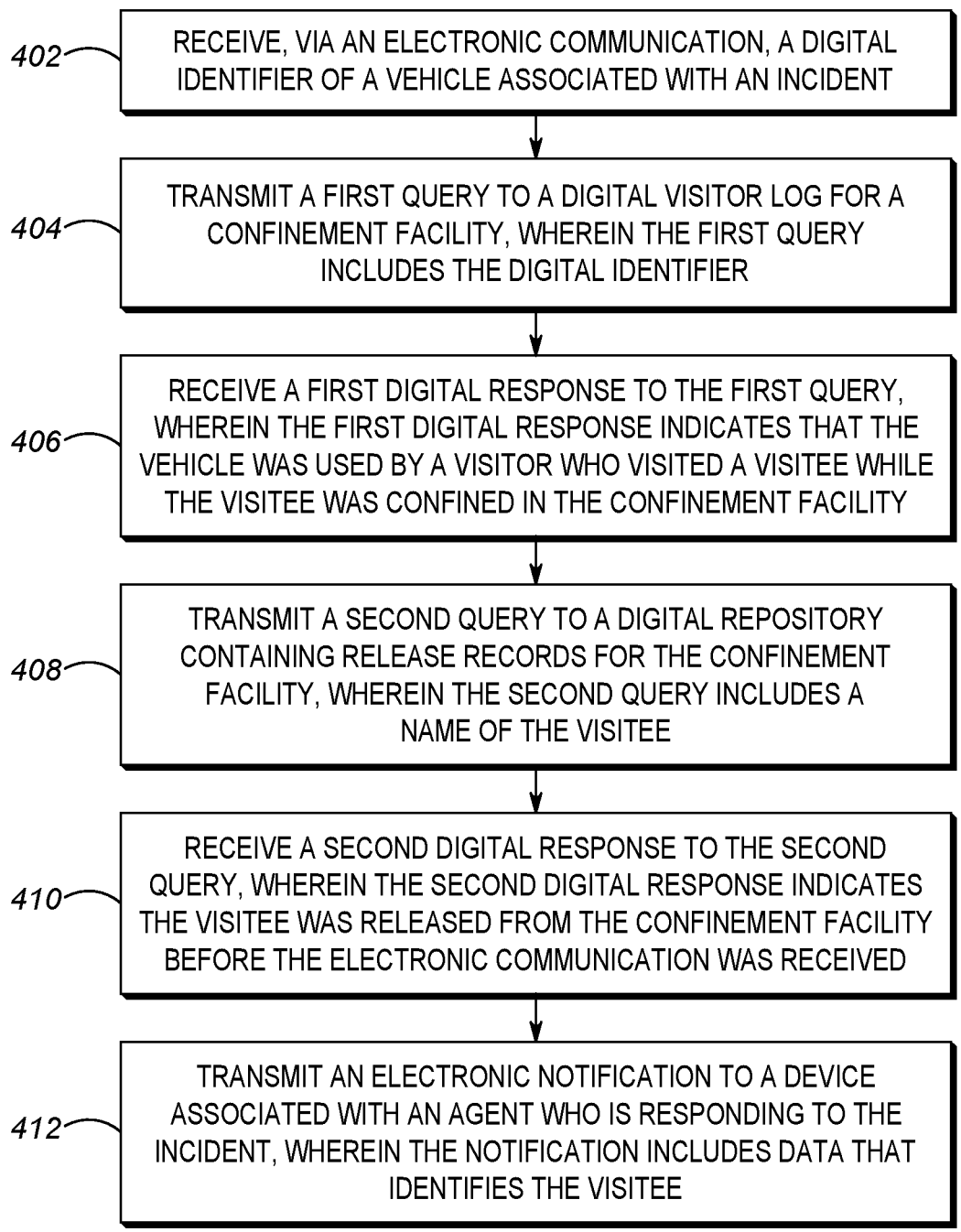
FIG. 4 also illustrates functionality for systems disclosed herein, according to one example.

FIG. 4 also illustrates functionality 400 for systems disclosed herein, according to one example. The functionality 400 does not have to be performed in the exact sequence shown. Also, various blocks may be performed in parallel rather than in sequence. Accordingly, the elements of the functionality 400 are referred to herein as "blocks" rather than "steps." The functionality 400 can be executed as instructions on a machine (e.g., by one or more processors), where the instructions are stored on a transitory or non-transitory computer-readable storage medium. While only six blocks are shown in the functionality 400, the functionality 400 may comprise other actions described herein. Also, in some examples, some of the blocks shown in the functionality 400 may be omitted without departing from the spirit and scope of this disclosure.

As shown in block 402, the functionality 400 includes receiving, via an electronic communication, a digital identifier of a vehicle associated with an incident. The digital identifier may be a license plate number, a digital image of a license plate attached to the vehicle, a VIN number, a digital image of a VIN number located on the vehicle, or some other digital identifier. The electronic communication may be received via an electronic communications network.

As shown in block 404, the functionality 400 includes transmitting a first query to a digital visitor log for a confinement facility, wherein the first query includes the digital identifier. The confinement facility may be a jail, a prison, a penitentiary, a psychiatric hospital, or some other institution where people may be confined. The first query may be transmitted via an electronic communications network.

As shown in block 406, the functionality 400 includes receiving a first digital response to the first query, wherein the first digital response indicates that the vehicle was used by a visitor who visited a visitee while the visitee was confined in the confinement facility. The digital response to the first query provides the name of the visitee. The digital response to the first query may be received via an electronic communications network.

As shown in block 408, the functionality 400 includes transmitting a second query to a digital repository containing release records for the confinement facility, wherein the second query includes a name of the visitee. The second query may be transmitted to the digital repository via an electronic communications network.

As shown in block 410, the functionality 400 includes receiving a second digital response to the second query, wherein the second digital response indicates the visitee was released from the confinement facility before the electronic communication was received. The second digital response may be received via an electronic communications network.

As shown in block 412, the functionality 300 includes transmitting an electronic notification to a device associated with an agent who is responding to the incident, wherein the notification includes data that identifies the visitee. The data that identifies the visitee may comprise the visitee's name, a digital image of the visitee, and other data that may be used to identify the visitee. The electronic notification may further indicate a type of a previous event that involved the visitee, wherein the visitee was confined in the confinement facility as a result of the previous event. Prior to transmitting the electronic notification, the functionality 400 may also include verifying that an amount of time that elapsed between when the visitee was released from the confinement facility and when the electronic communication was received meets a threshold.

In addition, the electronic notification may further include a prescriptive action for the agent based on a type of the previous event. For example, if the type of the previous event indicates that the visitee has been associated with illicit use of a substance, the prescriptive action may include bringing a medication that can be used to counteract an effect of the substance, refraining from an action that is likely to trigger aggressive behavior in persons who are under the influence of the substance, or refraining from applying a force technique that is likely to be ineffective for subduing persons who are under the influence of the substance.

In another example, if the type of the previous event indicates that the visitee suffers from a mental illness, the prescriptive action may include bringing a medication that can be used to counteract an effect of the mental illness, refraining from an action that is likely to trigger aggressive behavior in persons who suffer from the mental illness, or refraining from applying a force technique that is likely to be ineffective for subduing persons who suffer from the mental illness.

The functionality 400 may further include determining a risk score based on a type of the previous event and a type of the incident; and upon determining that the risk score satisfies a predefined condition, sending an additional electronic notification to the device associated with the agent. The additional notification may advise the agent to request that additional agents assist the agent in responding to the call.

Figure 5:
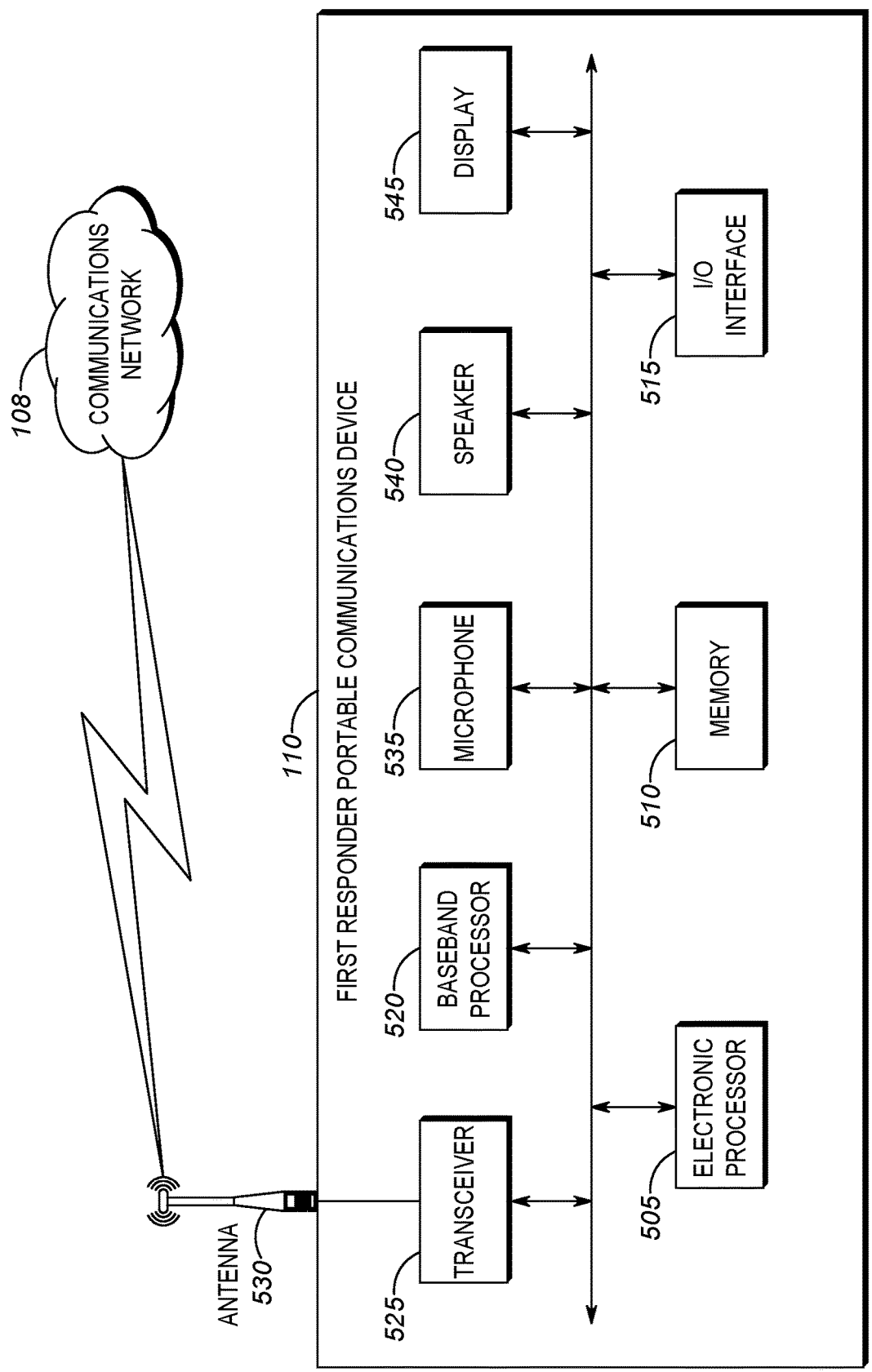
FIG. 5 illustrates an example of a portable communications device used in the systems described herein, according to one example.

It will be understood that each block of FIGS. 4-5, as well as combinations of those blocks, can be implemented by computer program instructions. These computer program instructions may be provided to a processor of a general purpose computer, special purpose computer, or other programmable data processing apparatus to produce a special purpose and unique machine, such that the instructions, which execute via the processor of the computer or other programmable data processing apparatus, create means for implementing the functions and actions specified in the blocks. In some examples, the functionality and processes set forth herein do not have to be performed in the exact sequences shown. Likewise, various blocks may be performed in parallel rather than in sequence. Accordingly, the elements of the functionality and processes are referred to herein as "blocks" rather than "steps."

These computer program instructions may also be stored in a computer-readable memory that can direct a computer or other programmable data processing apparatus to function in a particular manner, such that the instructions stored in the computer-readable memory produce an article of manufacture including instructions which implement the functionality and processes specified in the blocks.

The computer program instructions may also be loaded onto a computer or other programmable data processing apparatus that may be on or off-premises, or may be accessed via the cloud in any of a software as a service (SaaS), platform as a service (PaaS), or infrastructure as a service (IaaS) architecture so as to cause a series of operational blocks to be performed on the computer or other programmable apparatus to produce a computer-implemented process such that the instructions which execute on the computer or other programmable apparatus provide blocks for implementing the functions and actions specified the figures. It is contemplated that any part of any aspect or example discussed in this specification can be implemented or combined with any part of any other aspect or example discussed in this specification.

FIG. 5 illustrates an example of the portable communications device 110 in more detail, according to one example. In some of the examples described herein, the portable communications device 110 is a smart telephone. However, in other examples, the portable communications device 110 may be a cellular telephone, a satellite phone, a smart watch, a tablet computer, a personal digital assistant (PDA), a portable radio, a converged device (including both landmobile radio and cellular components), or another device that includes or is capable of being coupled to a network modem or components to enable wireless network communications (such as an amplifier, antenna, etc.) on cellular, land mobile, satellite, or other wireless communications networks.

In the example illustrated, the portable communications device 110 is a wireless communications device, which includes an electronic processor 505, a memory 510, an input/output interface 515, a baseband processor 520, a transceiver 525, an antenna 530, a microphone 535, a loudspeaker 540, and a display 545. The illustrated components, along with other various modules and components are coupled to each other by or through one or more control buses or data buses that enable communication therebetween (for example, a communication bus 560). In some examples, the portable communications device 110 includes fewer or additional components in configurations different from that illustrated in FIG. 5.

The electronic processor 505 obtains and provides information (for example, from the memory 510 and/or the input/output interface 515) and processes the information by executing one or more software instructions or modules that are capable of being stored, for example, in a random access memory ("RAM") area of the memory 510, a read only memory ("ROM") of the memory 510, or another non-transitory computer readable medium (not shown). The software can include firmware, one or more applications, program data, filters, rules, one or more program modules, and other executable instructions. The electronic processor 505 is configured to retrieve from the memory 510 and execute, among other things, software related to the control processes and methods described herein (for example, the action-guidance engine 150).

The memory 510 can include one or more non-transitory computer-readable media and includes a program storage area and a data storage area. The program storage area and the data storage area can include combinations of different types of memory, as described herein. In the example illustrated, the memory 510 may store, among other things, a digital identifier of a vehicle, an electronic query, and a risk score (described in detail above).

The input/output interface 515 is configured to receive input and to provide system output. The input/output interface 515 obtains information and signals from, and provides information and signals to, devices both internal and external to the portable communications device 110 (e.g., over one or more wired and/or wireless connections).

The electronic processor 505 is configured to control the baseband processor 520 and the transceiver 525 to transmit and receive radio frequency signals (for example, encoded with audio) to and from the portable communications device 110. The baseband processor 520 encodes and decodes digital data (including digitized audio signals) sent and received by the transceiver 525. The transceiver 525 transmits and receives radio signals to and from, for example, the communications network 108 (or another wireless network) using the antenna 530. The electronic processor 505, the baseband processor 520, and the transceiver 525 may include various digital and analog components (for example, digital signal processors, high band filters, low band filters, and the like), which for brevity are not described herein and which may be implemented in hardware, software, or a combination of both. In some examples, the transceiver 525 includes a combined transmitter-receiver component. In other examples, the transceiver 525 includes separate transmitter and receiver components.

The microphone 535 is a transducer capable of sensing sound, converting the sound to electrical signals, and transmitting the electrical signals to the electronic processor 505. The electronic processor 505 processes the electrical signals received from the microphone 535 to produce an audio signal, which may be transmitted to other devices via the transceiver 525. The loudspeaker 540 is a transducer for reproducing sound from electrical signals (for example, generated from a received audio signal) received from the electronic processor 505. The microphone 535 and the loudspeaker 540 support both audible and inaudible frequencies. In some examples, the microphone 535, the loudspeaker 540, or both may be integrated in a single housing with the other components (for example, in a portable hand-held radio). In some examples, the microphone 535, the loudspeaker 540, or both are present in an accessory device (for example, a remote speaker microphone (RSM)) connected via a wired or wireless connection to the portable communications device 110.

The display 545 is a suitable display, for example, a liquid crystal display (LCD) touch screen, or an organic light-emitting diode (OLED) touch screen. In some examples, the portable communications device 110 implements a graphical user interface (GUI) (for example, generated by the electronic processor 505, from instructions and data stored in the memory 510, and presented on the display 545), that enables a user to interact with the portable communications device 110.

In some examples, the telephone 118, although having distinct functions and capabilities, includes hardware and software having a similar configuration as the portable communications device 110.

Examples

The following additional examples are included below to highlight several aspects of the systems and processes described herein. However, the scope of the disclosure is not limited to these additional examples or the other examples described herein.

Example 1 includes a system comprising one or more processors and a memory containing instructions thereon which, when executed by the one or more processors, cause the processors to perform a set of actions comprising: receiving a phone call at a public safety access point (PSAP); transmitting a first query to a digital visitor log for a confinement facility, wherein the first query includes name associated with the call; receiving a first digital response to the first query, wherein the first digital response indicates that a visitor identified by the name associated with the call visited a visitee at the confinement facility while the visitee was confined at the confinement facility; transmitting a second query to a digital repository containing release records for the confinement facility, wherein the second query includes a name of the visitee; receiving a second digital response to the second query, wherein the second digital response indicates the visitee was released from the confinement facility before the call was received; and transmitting an electronic notification to a device associated with an agent who is responding to the call, wherein the electronic notification includes data that identifies the visitee Example 2 includes the system of example 1, wherein the electronic notification further indicates a type of a previous event that involved the visitee, wherein the visitee was confined in the confinement facility as a result of the previous event.

Example 3 includes the system of example 2, wherein the electronic notification further includes a prescriptive action for the agent based on a type of the previous event.

Example 4 includes the system of example 2 or 3, wherein the set of actions further comprises: determining a risk score based on a type of the previous event and a type of an incident reported in the call; and upon determining that the risk score satisfies a predefined condition, sending an additional electronic notification to the device associated with the agent, wherein the additional notification advises the agent to request that additional agents assist the agent in responding to the call.

Example 5 includes the system of example 3 or 4, wherein the type of the previous event indicates that the visitee has been associated with illicit use of a substance, and wherein the prescriptive action includes at least one of: bringing a medication that can be used to counteract an effect of the substance; refraining from an action that is likely to trigger aggressive behavior in persons who are under an influence of the substance; or refraining from applying a force technique that is likely to be ineffective for subduing persons who are under the influence of the sub stance.

Example 6 includes the system of example 3, 4, or 5, wherein the type of the previous event indicates that the visitee suffers from a mental illness, and wherein the prescriptive action includes at least one of: bringing a medication that can be used to counteract an effect of the mental illness; refraining from an action that is likely to trigger aggressive behavior in persons who suffer from the mental illness; or refraining from applying a force technique that is likely to be ineffective for subduing persons who suffer from the mental illness.

Example 7 includes the system of example 1, 2, 3, 4, 5, or 6, wherein the set of actions further comprises: prior to transmitting the electronic notification, verifying that an amount of time that elapsed between when the visitee was released from the confinement facility and when the call was received meets a threshold.

Example 8 includes a system comprising one or more processors and a memory containing instructions thereon which, when executed by the one or more processors, cause the processors to perform a set of actions comprising: receiving, via an electronic communication, a digital identifier of a vehicle associated with an incident; transmitting a first query to a digital visitor log for a confinement facility, wherein the first query includes the digital identifier; receiving a first digital response to the first query, wherein the first digital response indicates that the vehicle was used by a visitor who visited a visitee while the visitee was confined in the confinement facility; transmitting a second query to a digital repository containing release records for the confinement facility, wherein the second query includes a name of the visitee; receiving a second digital response to the second query, wherein the second digital response indicates the visitee was released from the confinement facility before the electronic communication was received; and transmitting an electronic notification to a device associated with an agent who is responding to the incident, wherein the electronic notification includes data that identifies the visitee.

Example 9 includes system of example 8, wherein the electronic notification further indicates a type of a previous event that involved the visitee, wherein the visitee was confined in the confinement facility as a result of the previous event.

Example 10 includes the system of example 9, wherein the electronic notification further includes a prescriptive action for the agent based on a type of the previous event.

Example 11 includes the system of example 9 or 10, wherein the set of actions further comprises: determining a risk score based on a type of the previous event and a type of the incident; and upon determining that the risk score satisfies a predefined condition, sending an additional electronic notification to the device associated with the agent, wherein the additional notification advises the agent to request that additional agents assist the agent in responding to the call.

Example 12 includes the system of example 10 or 11, wherein the type of the previous event indicates that the visitee has been associated with illicit use of a substance, and wherein the prescriptive action includes at least one of: bringing a medication that can be used to counteract an effect of the substance; refraining from an action that is likely to trigger aggressive behavior in persons who are under an influence of the substance; or refraining from applying a force technique that is likely to be ineffective for subduing persons who are under the influence of the sub stance.

Example 13 includes the system of example 10, 11, or 12, wherein the type of the previous event indicates that the visitee suffers from a mental illness, and wherein the prescriptive action includes at least one of: bringing a medication that can be used to counteract an effect of the mental illness; refraining from an action that is likely to trigger aggressive behavior in persons who suffer from the mental illness; or refraining from applying a force technique that is likely to be ineffective for subduing persons who suffer from the mental illness.

Example 14 includes the system of example 8, 9, 10, 11, 12, or 13, wherein the set of actions further comprises: prior to transmitting the electronic notification, verifying that an amount of time that elapsed between when the visitee was released from the confinement facility and when the electronic communication was received meets a threshold.

Example 15 includes a method comprising: receiving a phone call at a public safety access point (PSAP); transmitting a first query to a digital visitor log for a confinement facility, wherein the first query includes name associated with the call; receiving a first digital response to the first query, wherein the first digital response indicates that a visitor identified by the name associated with the call visited a visitee at the confinement facility while the visitee was confined at the confinement facility; transmitting a second query to a digital repository containing release records for the confinement facility, wherein the second query includes a name of the visitee; receiving a second digital response to the second query, wherein the second digital response indicates the visitee was released from the confinement facility before the call was received; and transmitting an electronic notification to a device associated with an agent who is responding to the call, wherein the electronic notification includes data that identifies the visitee Example 16 includes the method of example 15, wherein the electronic notification further indicates a type of a previous event that involved the visitee, wherein the visitee was confined in the confinement facility as a result of the previous event.

Example 17 includes the method of example 16, wherein the electronic notification further includes a prescriptive action for the agent based on a type of the previous event.

Example 18 includes the method of example 16 or 17, wherein the method further comprises: determining a risk score based on a type of the previous event and a type of an incident reported in the call; and upon determining that the risk score satisfies a predefined condition, sending an additional electronic notification to the device associated with the agent, wherein the additional notification advises the agent to request that additional agents assist the agent in responding to the call.

Example 19 includes the method of example 17 or 18, wherein the type of the previous event indicates that the visitee has been associated with illicit use of a substance, and wherein the prescriptive action includes at least one of: bringing a medication that can be used to counteract an effect of the substance; refraining from an action that is likely to trigger aggressive behavior in persons who are under an influence of the substance; or refraining from applying a force technique that is likely to be ineffective for subduing persons who are under the influence of the sub stance.

Example 20 includes the method of example 17, 18, or 19, wherein the type of the previous event indicates that the visitee suffers from a mental illness, and wherein the prescriptive action includes at least one of: bringing a medication that can be used to counteract an effect of the mental illness; refraining from an action that is likely to trigger aggressive behavior in persons who suffer from the mental illness; or refraining from applying a force technique that is likely to be ineffective for subduing persons who suffer from the mental illness.

Example 21 includes the method of example 15, 16, 17, 18, 19, or 20, wherein the set of actions further comprises: prior to transmitting the electronic notification, verifying that an amount of time that elapsed between when the visitee was released from the confinement facility and when the call was received meets a threshold.

Example 22 includes a method comprising: receiving, via an electronic communication, a digital identifier of a vehicle associated with an incident; transmitting a first query to a digital visitor log for a confinement facility, wherein the first query includes the digital identifier; receiving a first digital response to the first query, wherein the first digital response indicates that the vehicle was used by a visitor who visited a visitee while the visitee was confined in the confinement facility; transmitting a second query to a digital repository containing release records for the confinement facility, wherein the second query includes a name of the visitee; receiving a second digital response to the second query, wherein the second digital response indicates the visitee was released from the confinement facility before the electronic communication was received; and transmitting an electronic notification to a device associated with an agent who is responding to the incident, wherein the electronic notification includes data that identifies the visitee.

Example 23 includes method of example 22, wherein the electronic notification further indicates a type of a previous event that involved the visitee, wherein the visitee was confined in the confinement facility as a result of the previous event.

Example 24 includes the method of example 23, wherein the electronic notification further includes a prescriptive action for the agent based on a type of the previous event.

Example 25 includes the method of example 23 or 24, wherein the method further comprises: determining a risk score based on a type of the previous event and a type of the incident; and upon determining that the risk score satisfies a predefined condition, sending an additional electronic notification to the device associated with the agent, wherein the additional notification advises the agent to request that additional agents assist the agent in responding to the call.

Example 26 includes the method of example 24 or 25, wherein the type of the previous event indicates that the visitee has been associated with illicit use of a substance, and wherein the prescriptive action includes at least one of: bringing a medication that can be used to counteract an effect of the substance; refraining from an action that is likely to trigger aggressive behavior in persons who are under an influence of the substance; or refraining from applying a force technique that is likely to be ineffective for subduing persons who are under the influence of the substance.

Example 27 includes the method of example 24, 25, or 26, wherein the type of the previous event indicates that the visitee suffers from a mental illness, and wherein the prescriptive action includes at least one of: bringing a medication that can be used to counteract an effect of the mental illness; refraining from an action that is likely to trigger aggressive behavior in persons who suffer from the mental illness; or refraining from applying a force technique that is likely to be ineffective for subduing persons who suffer from the mental illness.

Example 28 includes the method of example 22, 23, 24, 25, 26, or 27, wherein the method further comprises: prior to transmitting the electronic notification, verifying that an amount of time that elapsed between when the visitee was released from the confinement facility and when the electronic communication was received meets a threshold.

Example 29 includes a non-transitory computer-readable storage medium containing instructions that, when executed by one or more processors, perform a set of actions comprising: receiving a phone call at a public safety access point (PSAP); transmitting a first query to a digital visitor log for a confinement facility, wherein the first query includes name associated with the call; receiving a first digital response to the first query, wherein the first digital response indicates that a visitor identified by the name associated with the call visited a visitee at the confinement facility while the visitee was confined at the confinement facility; transmitting a second query to a digital repository containing release records for the confinement facility, wherein the second query includes a name of the visitee; receiving a second digital response to the second query, wherein the second digital response indicates the visitee was released from the confinement facility before the call was received; and transmitting an electronic notification to a device associated with an agent who is responding to the call, wherein the electronic notification includes data that identifies the visitee Example 30 includes the non-transitory computer-readable storage medium of example 29, wherein the electronic notification further indicates a type of a previous event that involved the visitee, wherein the visitee was confined in the confinement facility as a result of the previous event.

Example 31 includes the non-transitory computer-readable storage medium of example 30, wherein the electronic notification further includes a prescriptive action for the agent based on a type of the previous event.

Example 32 includes the non-transitory computer-readable storage medium of example 30 or 31, wherein the set of actions further comprises: determining a risk score based on a type of the previous event and a type of an incident reported in the call; and upon determining that the risk score satisfies a predefined condition, sending an additional electronic notification to the device associated with the agent, wherein the additional notification advises the agent to request that additional agents assist the agent in responding to the call.

Example 33 includes the non-transitory computer-readable storage medium of example 31 or 32, wherein the type of the previous event indicates that the visitee has been associated with illicit use of a substance, and wherein the prescriptive action includes at least one of: bringing a medication that can be used to counteract an effect of the substance; refraining from an action that is likely to trigger aggressive behavior in persons who are under an influence of the substance; or refraining from applying a force technique that is likely to be ineffective for subduing persons who are under the influence of the substance.

Example 34 includes the non-transitory computer-readable storage medium of example 31, 32, or 33, wherein the type of the previous event indicates that the visitee suffers from a mental illness, and wherein the prescriptive action includes at least one of: bringing a medication that can be used to counteract an effect of the mental illness; refraining from an action that is likely to trigger aggressive behavior in persons who suffer from the mental illness; or refraining from applying a force technique that is likely to be ineffective for subduing persons who suffer from the mental illness.

Example 35 includes the non-transitory computer-readable storage medium of example 29, 30, 31, 32, 33, or 34, wherein the set of actions further comprises: prior to transmitting the electronic notification, verifying that an amount of time that elapsed between when the visitee was released from the confinement facility and when the call was received meets a threshold.

Example 36 includes a non-transitory computer-readable storage medium containing instructions that, when executed by one or more processors, perform a set of actions comprising: receiving, via an electronic communication, a digital identifier of a vehicle associated with an incident; transmitting a first query to a digital visitor log for a confinement facility, wherein the first query includes the digital identifier; receiving a first digital response to the first query, wherein the first digital response indicates that the vehicle was used by a visitor who visited a visitee while the visitee was confined in the confinement facility; transmitting a second query to a digital repository containing release records for the confinement facility, wherein the second query includes a name of the visitee; receiving a second digital response to the second query, wherein the second digital response indicates the visitee was released from the confinement facility before the electronic communication was received; and transmitting an electronic notification to a device associated with an agent who is responding to the incident, wherein the electronic notification includes data that identifies the visitee.

Example 37 includes the non-transitory computer-readable storage medium of example 36, wherein the electronic notification further indicates a type of a previous event that involved the visitee, wherein the visitee was confined in the confinement facility as a result of the previous event.

Example 38 includes the non-transitory computer-readable storage medium of example 37, wherein the electronic notification further includes a prescriptive action for the agent based on a type of the previous event.

Example 39 includes the non-transitory computer-readable storage medium of example 37 or 38, wherein the set of actions further comprises: determining a risk score based on a type of the previous event and a type of the incident; and upon determining that the risk score satisfies a predefined condition, sending an additional electronic notification to the device associated with the agent, wherein the additional notification advises the agent to request that additional agents assist the agent in responding to the call.

Example 40 includes the non-transitory computer-readable storage medium of example 38 or 39, wherein the type of the previous event indicates that the visitee has been associated with illicit use of a substance, and wherein the prescriptive action includes at least one of: bringing a medication that can be used to counteract an effect of the substance; refraining from an action that is likely to trigger aggressive behavior in persons who are under an influence of the substance; or refraining from applying a force technique that is likely to be ineffective for subduing persons who are under the influence of the substance.

Example 41 includes the non-transitory computer-readable storage medium of example 38, 39, or 40, wherein the type of the previous event indicates that the visitee suffers from a mental illness, and wherein the prescriptive action includes at least one of: bringing a medication that can be used to counteract an effect of the mental illness; refraining from an action that is likely to trigger aggressive behavior in persons who suffer from the mental illness; or refraining from applying a force technique that is likely to be ineffective for subduing persons who suffer from the mental illness.

Example 42 includes the non-transitory computer-readable storage medium of example 36, 37, 38, 39, 40, or 41, wherein the set of actions further comprises: prior to transmitting the electronic notification, verifying that an amount of time that elapsed between when the visitee was released from the confinement facility and when the electronic communication was received meets a threshold.

As should be apparent from this detailed description above, the operations and functions described herein are sufficiently complex as to require their implementation on a computer system, and cannot be performed, as a practical matter, in the human mind. Systems such as those set forth herein are understood as requiring and providing speed (time is of the essence for first responders) and accuracy and complexity management that are not obtainable by human mental steps, in addition to the inherently digital nature of such operations (e.g., a human mind cannot interface directly with RAM or other digital storage, cannot transmit or receive electronic messages, electronically encoded video, or electronically encoded audio, etc., among other features and functions set forth herein).

In the foregoing specification, specific examples have been described. However, one of ordinary skill in the art will appreciate that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing," or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially," "essentially," "approximately," "about," or any other version thereof, are defined as being close to as understood by one of ordinary skill in the art, and in one non-limiting example the term is defined to be within 10%, in another example within 5%, in another example within 1%, and in another example within 0.5%. The term "one of," without a more limiting modifier such as "only one of," and when applied herein to two or more subsequently defined options such as "one of A and B" should be construed to mean an existence of any one of the options in the list alone (e.g., A alone or B alone) or any combination of two or more of the options in the list (e.g., A and B together).

A device or structure that is "configured" in a certain way is configured in at least that way, but may also be configured in ways that are not listed.

The terms "coupled," "coupling," or "connected" as used herein can have several different meanings depending on the context in which these terms are used. For example, the terms coupled, coupling, or connected can have a mechanical or electrical connotation. For example, as used herein, the terms coupled, coupling, or connected can indicate that two elements or devices are directly connected to one another or connected to one another through intermediate elements or devices via an electrical element, electrical signal or a mechanical element depending on the particular context.

It will be appreciated that some examples may comprise one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an example can be implemented as a computer-readable storage medium having computer readable code stored thereon for programming a computer (e.g., comprising a processor) to perform a method as described and claimed herein. Any suitable computer-usable or computer readable medium may be utilized. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. In the context of this document, a computer-usable or computer-readable medium may be any medium that can contain, store, communicate, propagate, or transport the program for use by or in connection with the instruction execution system, apparatus, or device.

Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation. For example, computer program code for carrying out operations of various examples may be written in an object oriented programming language such as Java, Smalltalk, C++, Python, or the like. However, the computer program code for carrying out operations of various examples may also be written in conventional procedural programming languages, such as the "C" programming language or similar programming languages. The program code may execute entirely on a computer, partly on the computer, as a stand-alone software package, partly on the computer and partly on a remote computer or server or entirely on the remote computer or server. In the latter scenario, the remote computer or server may be connected to the computer through a local area network (LAN) or a wide area network (WAN), or the connection may be made to an external computer (for example, through the Internet using an Internet Service Provider).

The Abstract of the Disclosure is provided to allow the reader to quickly ascertain the nature of the technical disclosure. It is transmitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A system comprising:
   one or more processors; and
   a memory storing instructions thereon which, when executed by the one or more processors, cause the one or more processors to perform a set of actions comprising:
   receiving a name associated with a communication received at a public safety access point (PSAP);
   transmitting a first query to a digital data repository comprising a digital visitor log for a confinement facility, wherein the first query includes the name associated with the communication;
   receiving a first digital response to the first query, wherein the first digital response specifies a visitor identified by the name associated with the communication that visited a visitee at the confinement facility while the visitee was confined at the confinement facility;
   transmitting a second query to a digital repository comprising release records for the confinement facility, wherein the second query includes a name of the visitee;
   receiving a second digital response to the second query, wherein the second digital response indicates the visitee was released from the confinement facility before the communication was received; and
   transmitting an electronic notification to a device associated with an agent who is responding to the communication, wherein the electronic notification includes data that identifies the visitee.

2. The system of claim 1, wherein the electronic notification further indicates a type of a previous event that involved the visitee, and wherein the visitee was confined in the confinement facility as a result of the previous event.

3. The system of claim 2, wherein the electronic notification further includes a prescriptive action for the agent based on a type of the previous event.

4. The system of claim 2, wherein the set of actions further comprises:
   determining a risk score based on a type of the previous event and a type of an incident reported in the communication; and
   upon determining that the risk score satisfies a predefined condition, sending an additional electronic notification to the device associated with the agent, wherein the additional electronic notification advises the agent to request that additional agents assist the agent in responding to the communication.

5. The system of claim 3, wherein the type of the previous event indicates that the visitee has been associated with illicit use of a substance, and wherein the prescriptive action includes at least one of:
bringing a medication that can be used to counteract an effect of the substance;
refraining from an action that is likely to trigger aggressive behavior in persons who are under an influence of the substance; or
refraining from applying a force technique that is likely to be ineffective for subduing persons who are under the influence of the substance.

6. The system of claim 3, wherein the type of the previous event indicates that the visitee suffers from a mental illness, and wherein the prescriptive action includes at least one of:
bringing a medication that can be used to counteract an effect of the mental illness;
refraining from an action that is likely to trigger aggressive behavior in persons who suffer from the mental illness; or
refraining from applying a force technique that is likely to be ineffective for subduing persons who suffer from the mental illness.

7. The system of claim 1, wherein the set of actions further comprises:
prior to transmitting the electronic notification, verifying that an amount of time that elapsed between when the visitee was released from the confinement facility and when the communication was received meets a threshold.

8. A method comprising:
receiving a name associated with a communication received at a public safety access point (PSAP);
transmitting a first query to a digital repository comprising a digital visitor log for a confinement facility, wherein the first query includes the name associated with the communication;
receiving a first digital response to the first query, wherein the first digital response specifies a visitor identified by the name associated with the communication that visited a visitee at the confinement facility while the visitee was confined at the confinement facility;
transmitting a second query to a digital repository comprising release records for the confinement facility, wherein the second query includes a name of the visitee;
receiving a second digital response to the second query, wherein the second digital response indicates the visitee was released from the confinement facility before the communication was received; and
transmitting an electronic notification to a device associated with an agent who is responding to the communication, wherein the electronic notification includes data that identifies the visitee.

9. The method of claim 8, wherein the electronic notification further indicates a type of a previous event that involved the visitee, and wherein the visitee was confined in the confinement facility as a result of the previous event.

10. The method of claim 9, wherein the electronic notification further includes a prescriptive action for the agent based on a type of the previous event.

11. The method of claim 9, further comprising:
determining a risk score based on a type of the previous event and a type of an incident reported in the communication; and
upon determining that the risk score satisfies a predefined condition, sending an additional electronic notification to the device associated with the agent, wherein the additional electronic notification advises the agent to request that additional agents assist the agent in responding to the communication.

12. The method of claim 10, wherein the type of the previous event indicates that the visitee has been associated with illicit use of a substance, and wherein the prescriptive action includes at least one of:
bringing a medication that can be used to counteract an effect of the substance;
refraining from an action that is likely to trigger aggressive behavior in persons who are under an influence of the substance; or
refraining from applying a force technique that is likely to be ineffective for subduing persons who are under the influence of the substance.

13. The method of claim 10, wherein the type of the previous event indicates that the visitee suffers from a mental illness, and wherein the prescriptive action includes at least one of:
bringing a medication that can be used to counteract an effect of the mental illness;
refraining from an action that is likely to trigger aggressive behavior in persons who suffer from the mental illness; or
refraining from applying a force technique that is likely to be ineffective for subduing persons who suffer from the mental illness.

14. A non-transitory computer-readable storage medium storing instructions thereon which, when executed by a computing system, cause the computing system to perform a set of actions comprising:
receiving a name associated with a communication received at a public safety access point (PSAP);
transmitting a first query to a digital data repository comprising a digital visitor log for a confinement facility, wherein the first query includes the name associated with the communication;
receiving a first digital response to the first query, wherein the first digital response specifies a visitor identified by the name associated with the communication that visited a visitee at the confinement facility while the visitee was confined at the confinement facility;
transmitting a second query to a digital repository comprising release records for the confinement facility, wherein the second query includes a name of the visitee;
receiving a second digital response to the second query, wherein the second digital response indicates the visitee was released from the confinement facility before the communication was received; and
transmitting an electronic notification to a device associated with an agent who is responding to the communication, wherein the electronic notification includes data that identifies the visitee.

15. The non-transitory computer-readable storage medium of claim 14, wherein the electronic notification further indicates a type of a previous event that involved the visitee, and wherein the visitee was confined in the confinement facility as a result of the previous event.

16. The non-transitory computer-readable storage medium of claim 15, wherein the electronic notification further includes a prescriptive action for the agent based on a type of the previous event.

17. The non-transitory computer-readable storage medium of claim 15, wherein the set of actions further comprises:
   determining a risk score based on a type of the previous event and a type of an incident reported in the communication; and
   upon determining that the risk score satisfies a predefined condition, sending an additional electronic notification to the device associated with the agent, wherein the additional electronic notification advises the agent to request that additional agents assist the agent in responding to the communication.

18. The non-transitory computer-readable storage medium of claim 16, wherein the type of the previous event indicates that the visitee has been associated with illicit use of a substance, and wherein the prescriptive action includes at least one of:
   bringing a medication that can be used to counteract an effect of the substance;
   refraining from an action that is likely to trigger aggressive behavior in persons who are under an influence of the substance; or
   refraining from applying a force technique that is likely to be ineffective for subduing persons who are under the influence of the substance.

19. The non-transitory computer-readable storage medium of claim 16, wherein the type of the previous event indicates that the visitee suffers from a mental illness, and wherein the prescriptive action includes at least one of:
   bringing a medication that can be used to counteract an effect of the mental illness;
   refraining from an action that is likely to trigger aggressive behavior in persons who suffer from the mental illness; or
   refraining from applying a force technique that is likely to be ineffective for subduing persons who suffer from the mental illness.

20. The non-transitory computer-readable storage medium of claim 14, wherein the set of actions further comprises prior to transmitting the electronic notification, verifying that an amount of time that elapsed between when the visitee was released from the confinement facility and when the communication was received meets a threshold.

* * * * *